United States Patent
Crespo

(10) Patent No.: US 6,939,360 B2
(45) Date of Patent: Sep. 6, 2005

(54) EAR CLEANING APPLIANCE AND METHOD OF MANUFACTURE

(75) Inventor: Anthony K. Crespo, Morristown, TN (US)

(73) Assignee: Healthy Enterprises, Independence, MO (US)

( * ) Notice: Subject to any disclaimer, the term of this patent is extended or adjusted under 35 U.S.C. 154(b) by 437 days.

(21) Appl. No.: 10/050,343

(22) Filed: Jan. 16, 2002

(65) Prior Publication Data

US 2003/0135228 A1 Jul. 17, 2003

(51) Int. Cl.⁷ .............................................. A61F 11/00
(52) U.S. Cl. ...................................................... 606/162
(58) Field of Search ........................ 606/162, 159–161, 606/170, 172, 200, 110, 108, 107, 113

(56) References Cited

U.S. PATENT DOCUMENTS

| | | | | |
|---|---|---|---|---|
| 5,197,968 A | * | 3/1993 | Clement | 606/113 |
| 5,334,212 A | * | 8/1994 | Karell | 606/162 |
| 5,632,756 A | * | 5/1997 | Kruglick | 606/162 |
| 5,715,850 A | * | 2/1998 | Markgraaf | 606/162 |
| 5,888,199 A | * | 3/1999 | Karell et al. | 606/162 |
| 6,063,082 A | * | 5/2000 | DeVore et al. | 606/170 |
| 6,187,017 B1 | * | 2/2001 | Gregory, Jr. | 606/127 |
| 6,224,612 B1 | * | 5/2001 | Bates et al. | 606/114 |
| 6,264,664 B1 | * | 7/2001 | Avellanet | 606/127 |
| 6,270,510 B1 | * | 8/2001 | Westendorf | 606/162 |
| 6,626,915 B2 | * | 9/2003 | Leveillee | 606/113 |
| 6,736,826 B2 | * | 5/2004 | Begun | 606/162 |
| 6,776,786 B2 | * | 8/2004 | Kim | 606/162 |

* cited by examiner

Primary Examiner—Anhtuan T. Nguyen
Assistant Examiner—Jessica R. Baxter
(74) Attorney, Agent, or Firm—Pitts & Brittian, P.C.

(57) ABSTRACT

A disposable ear cleaning appliance comprising an elongated stem having a hollow cavity which opens outwardly from one end thereof, and a plurality, preferably four, flexible lengths of thermoplastic monofilament. These lengths of monofilament are joined at their outboard ends and extend therefrom to define a bulbous shape. At their respective outboard ends, the thermoplastic monofilaments are bonded by heat and pressure, for example, to form a flattened region which serves to partially stiffen the individual monofilaments adjacent the bonded region and for a relatively short distance therefrom. Thus when the monofilaments are bent into a bulbous configuration by applying pressure against their respective inboard ends to gather the inboard ends into a bundle, the individual monofilaments are placed in compression and tend to retain their bulbous configuration. The accumulated inboard ends of the several monofilaments are gathered into a bundle in which the monofilaments lie side by side in close packed relationship. This bundle of ends is inserted into the hollow cavity at the end of the stem and anchored therein as by sonic welding, adhesive or other suitable bonding technique.

7 Claims, 3 Drawing Sheets

EAR CLEANING APPLIANCE AND METHOD OF MANUFACTURE

FIELD OF INVENTION

This invention relates to appliances for cleaning foreign matter from the ear, particularly for removal of ear wax from the outer ear canal.

BACKGROUND OF INVENTION

Possibly the most commonly known ear cleaner is the appliance marketed under the tradename Q-Tip. This product comprises a wad of cotton fibers bonded onto one end of an elongated stem or handle. These products, however, suffer from multiple problems including a tendency of a user to insert the appliance too far into the ear canal and the tendency of the cotton fibers to dislodge and remain within the ear canal.

In any ear cleaning appliance, its is desired that the portion of the appliance which enters the ear canal be readily capable of grasping any encountered foreign matter and retain the same on the appliance for removal of the foreign matter when the appliance is withdrawn from the ear canal.

Moreover, it is desirable that the appliance not be so rigid as to be capable of doing serious damage to the ear when inserted into the ear canal. Further, desirably, the ear cleaning appliance is disposable after one use, hence its cost of production should be minimal. For this latter reason, not only the cost of the raw materials employed in the appliance is of concern, but the cost of the actual manufacture of the appliance is important.

SUMMARY OF INVENTION

In accordance with one aspect of the present invention, there is provided a disposable ear cleaning appliance comprising an elongated stem having a hollow cavity which opens outwardly from one end thereof, and a plurality, preferably four, flexible lengths of thermoplastic monofilament. These lengths of monofilament are joined at their outboard ends and extend therefrom to define a bulbous shape. At their respective outboard ends, the thermoplastic monofilaments are bonded by heat and pressure, for example, to form a flattened region which serves to partially stiffen the individual monofilaments adjacent the bonded region and for a relatively short distance therefrom. Thus when the monofilaments are bent into a bulbous configuration by applying pressure against their respective inboard ends to gather the inboard ends into a bundle, the individual monofilaments are placed in compression and tend to retain their bulbous configuration. The accumulated inboard ends of the several monofilaments are gathered into a bundle in which the monofilaments lie in side by side in close packed relationship. This bundle of ends is inserted into the hollow cavity at the end of the stem and anchored therein as by sonic welding, adhesive or other suitable bonding technique.

DETAILED DESCRIPTION OF THE INVENTION

Figure 1:
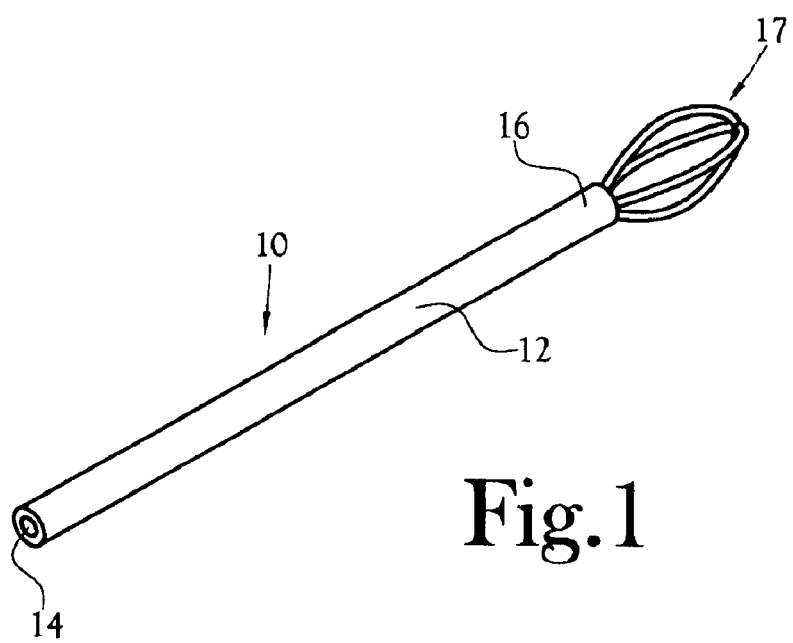
FIG. 1 is a representation of one embodiment of the appliance of the present invention.

Referring initially to FIG. 1, a preferred embodiment of the appliance 10 of the present invention comprises an elongated stem 12, which in the depicted embodiment is in the form of a hollow tube 14 suitable to be grasped between the thumb and finger(s) of a user's hand. Within one end 16 of the hollow tube, there is secured a cleaning head 17 adapted to enter the ear canal for the removal of foreign matter from the ear canal.

The stem 12 of the preferred embodiment of the present appliance comprises a hollow tube 14 about 6 cm long, and fabricated from a 15 gauge thermoplastic polymer, such as polypropylene. The outer diameter of the tube suitably is between about 0.002 and about 0.003 mm and the inner diameter is at least large enough to receive within an open end 16 thereof a side-by-side closed packed bundle 68 (FIG. 2) of four or more ends of monofilament of between 18 and 25 gauge polymeric monofilament. This stem is substantially rigid, and readily grasped between the thumb and one or more fingers of the user's hand for insertion of the head 17 into an ear canal and rotation of the stem and head while the head is within the ear canal. Preferably the stem is colored to provide ready visual recognition thereof. One suitable color is light blue, such as is typically employed in coloring of disposable medical supplies.

Figure 2:
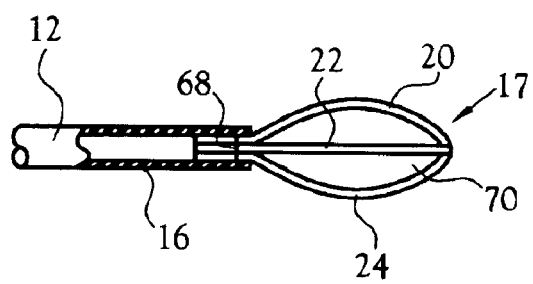
FIG. 2 is an enlarged side plan view of one end of the appliance depicted in FIG. 1.
Figure 3A:
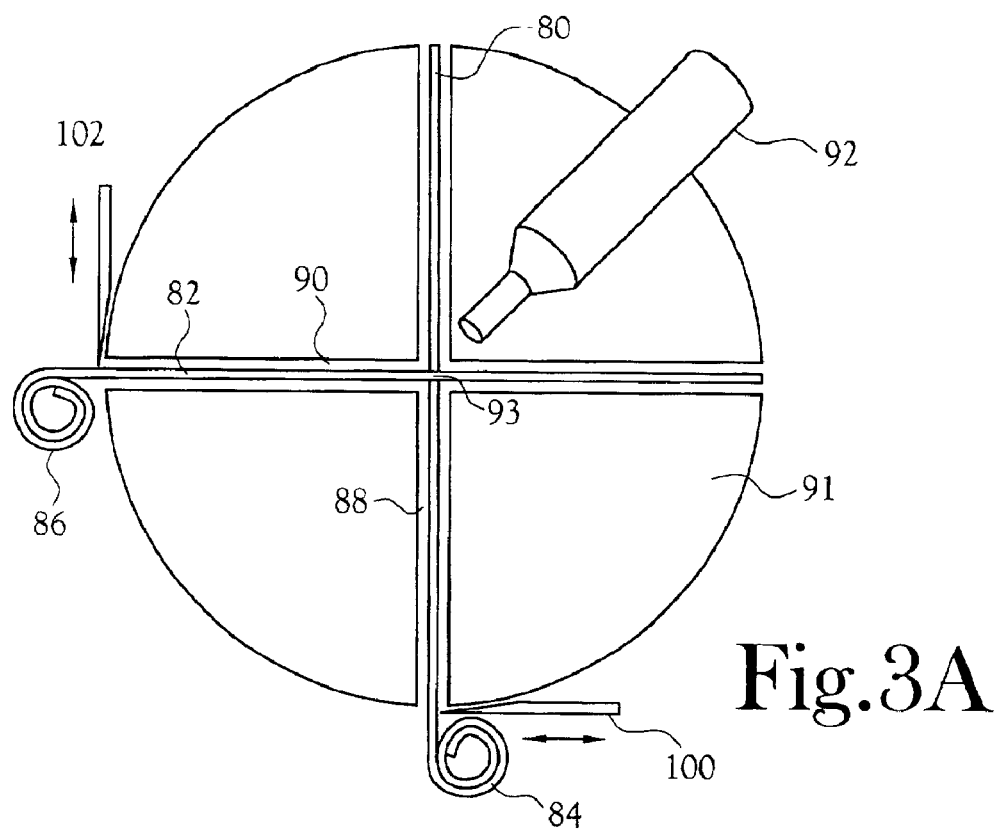
FIG. 3A is a schematic representation of a step in the manufacture of the appliance of the present invention.
Figure 3B:
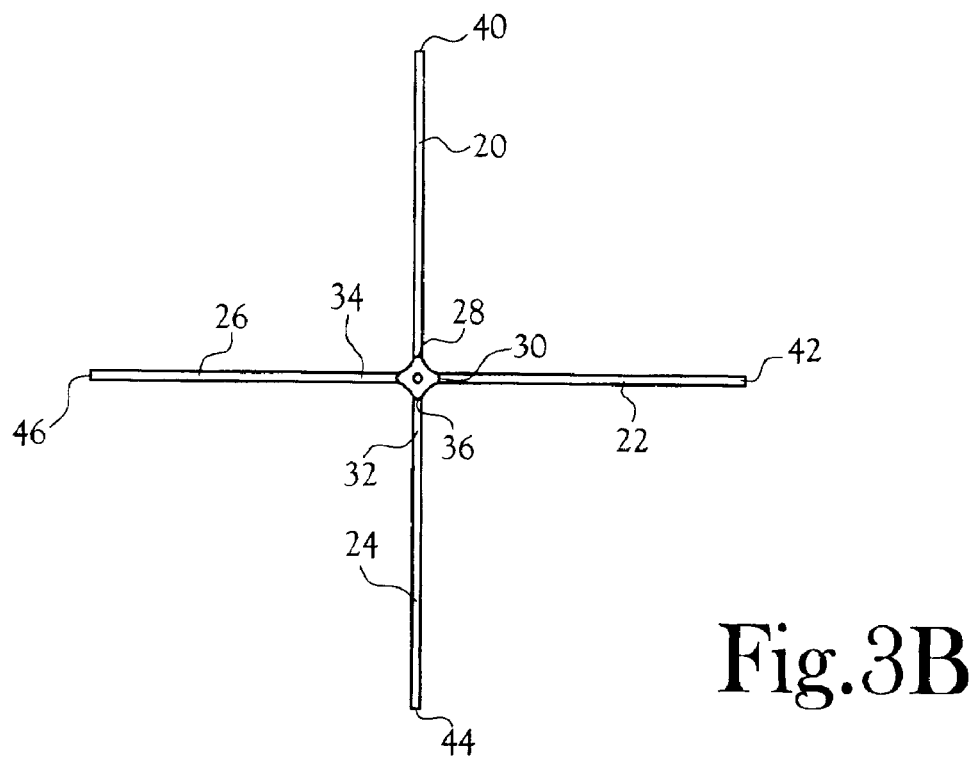
FIG. 3B is a schematic representation of a further step in the manufacture of the appliance of the present invention.
Figure 3C:
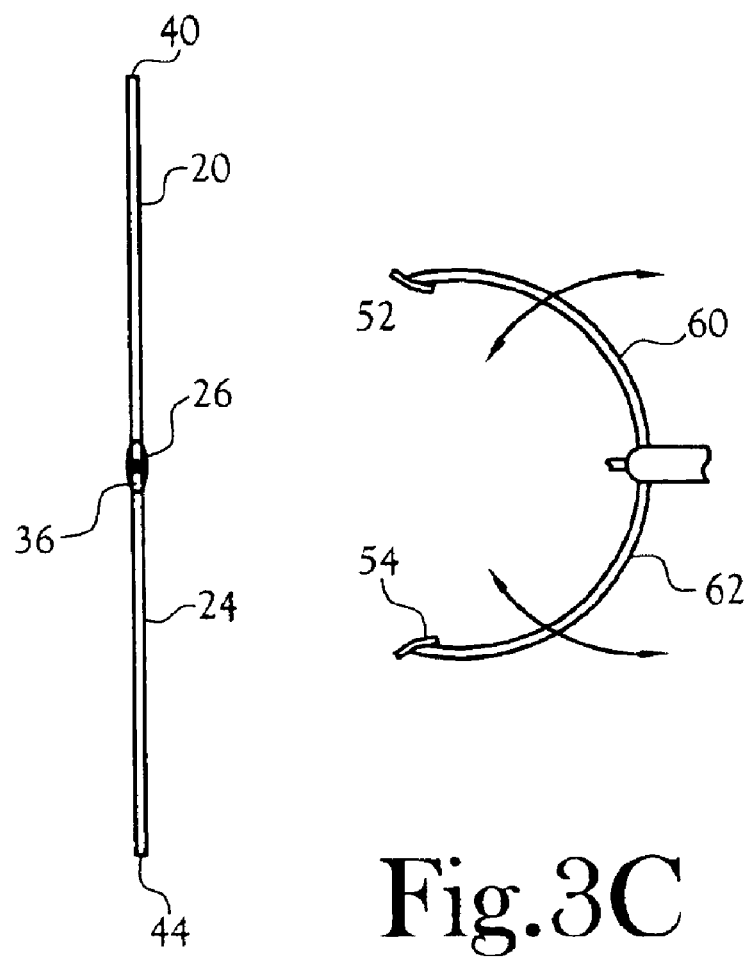
FIG. 3C is a schematic representation of a still further step in the manufacture of the appliance of the present invention.
Figure 3D:
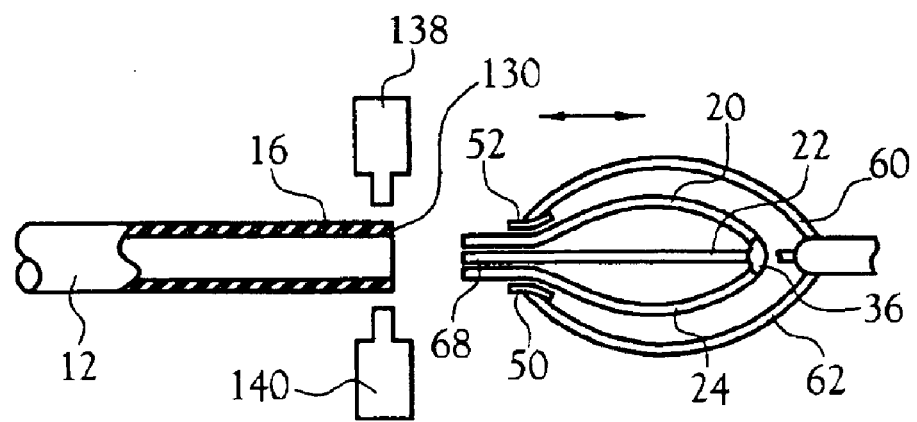
FIG. 3D is a schematic representation of an even further step in the manufacture of the appliance of the present invention.

As depicted in FIG. 2, the head 17 of the present appliance comprises a plurality, four in a preferred embodiment, of lengths of monofilament 20, 22, 24, and 26. Only three of the lengths are visible in FIGS. 2 and 3D, but all four are depicted in FIG. 3B. Each length suitably is about 1.5 cm long. As best seen in FIGS. 2 and 3B, the outboard ends 28, 30, 32, and 34 of the lengths of monofilament are bonded together, as by sonic welding, to define a central mass 36 of molten and then solidified polymer which extends from the central mass into at least a portion of the length of each length of monofilament thereby rigidifying that portion of each monofilament which is adjacent the central mass 36. Thus, the lengths of monofilament are not only bonded to each other at their outboard ends, each length of monofilament includes a portion thereof which resists bending of the monofilament adjacent its outboard end by reason of the migrated and solidified thermoplastic thereon. By reason of this rigidity imparted to the outboard ends of the lengths of monofilaments, it has been found possible to contact the inboard ends 40, 42, 44 and 46 with respective pressure pads 50, 52 which are mounted on respective swing arms 60, 62 and bring the inboard ends of the lengths of monofilament together into a bundle 68 wherein the several inboard ends of the monofilaments lie in side-by-side closed packed relationship to one another and thereby cause each of the monofilaments to bow outwardly from one another to define the bulbous cleaning head 17. It will be recognized that there is a like pressure pad and swing arm associated with each inboard end of monofilament even though only two such pressure pads and three such swing arms are depicted in the schematics of FIGS. 3C and 3D and that all four pressure pads and their respective swing arms function simultaneously to define the bundle of inboard ends of the lengths of monofilaments and, consequently, the bulbous nature of the head.

The bundle 68 of inboard ends of the several lengths of monofilament is received within the hollow end 16 of the stem a distance of about 5 mm and bonded in place, as by sonic welding or other suitable attachment means, thereby securely anchoring the head within the end 16 of the stem. By reason of the rigidity imparted to a portion of each length of monofilament adjacent its outboard end by the mass 36, once the inboard ends of the monofilaments are captured within the end of the stem, the individual monofilaments retain their bowed attitude. In turn, their collective bowed attitudes define the desired bulbous configuration of the head.

Figure 4:
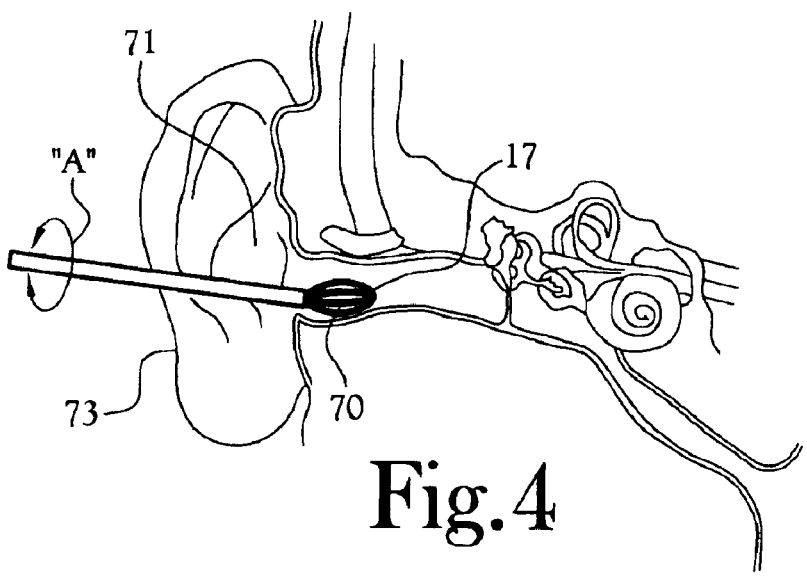
FIG. 4 is a representation of one use of the appliance of the present invention for cleaning the outer portion of an ear canal.

Referring to FIG. 4, by reason of the structure of the head described hereinabove, when the head is inserted into an ear canal, each monofilament is free to bend slightly and thereby conform to whatever surface the head may encounter within the ear canal, thereby permitting each portion of the irregular inner surface of the ear canal to be swept by rotating the stem of the appliance between the thumb and fingers of the user (See arrow "A" of FIG. 4. This action further serves to detach any foreign matter within the ear canal and collect the same on the surface of one or more of the lengths of monofilament, or between adjacent ones of the lengths of monofilaments, or within the interior region 70 of the bulbous head of the appliance. Upon withdrawal of the appliance from the ear canal, the captured foreign matter is likewise withdrawn form the ear canal. Moreover, the flexible nature of the individual lengths of monofilaments of the cleaning head permit the head to also be used to clean the outer surfaces 71 of the ear lobe 73 in like manner.

Limitation of the extent of insertion of the present appliance into the ear canal is provided by the user grasping the stem at a location immediately adjacent the end 16 of the stem whereupon the thumb and finger(s) of the user serve to not only limit the extent of insertion of the head into the ear canal, but also to closely control the degree of pressure being applied to the head. More specifically, when so grasped by a user, the opposite end 72 of the stem may rest on the finger(s) or side of the user's hand thereby providing stability of the stem and prevention of deleterious engagement of the stem with a sensitive portion of the ear. Moreover, such grasping position permits the user to sense the degree of pressure with which the head of the appliance is engaging the inner wall of the ear canal, as opposed to the situation where the stem is grasped at a location near its midpoint or near its end 72. Still further, the juncture of the end 16 of the stem with the bundle of monofilament ends provides a tactile sensory location for position of the user's thumb and finger(s) when grasping the present appliance for use thereof.

Referring to FIGS. 3A–3D, in one embodiment of a method for the manufacture of an appliance according to the present invention, first and second monofilaments 80 and 82, respectively, are fed from coiled rolls 84 and 86, respectively, into perpendicularly intersecting grooves 88,90 in a die 91 such that the monofilaments cross over one another at the midpoints 93 of the grooves. Each of the monofilaments is severed from its respective coil at its point of entry into a groove as by reciprocating knives 100,102. Thereupon, at the intersection of the monofilaments, they are bonded to one another by a sonic sealer 92 which applies pressure against the intersection of the filaments while heating the same to at least the fusion point of the thermoplastic. In the present instance, the pressure applied by the sonic sealer to the intersection of the monofilaments in the course of heating the monofilaments, substantially flattens the monofilaments causing the thermoplastic material to flow laterally away from the intersection of the monofilaments and thereby produce a substantial mass 36 (FIG. 3B) of molten thermoplastic material at the intersection. Under the influence of the applied pressure, this molten mass spreads laterally in a direction away from the mass and along the length of each of the monofilaments and when the heat is removed, the mass cools and solidifies. This action results in a stiffening of each of the monofilaments in the region thereof adjacent the central mass of solidified thermoplastic. As noted hereinabove, this mass of solidified thermoplastic is effective in limiting the degree of bowing of the lengths of monofilament into a bulbous head. Further, the bonding of the two initial lengths of monofilament 80 and 82 at their intersection, there are defined the aforesaid four lengths of monofilaments 20,22,24 and 26, each having its outboard end bonded to the outboard end of each other filament. Notably, as seen in FIG. 3B, the four monofilaments extend laterally away from their juncture of joinder in respective directions which are oriented at 90 degrees intervals about their juncture of joinder.

After bonding of the intersection of the monofilaments, the interim product depicted in FIG. 3B is formed into a bulbous configuration by contacting the outboard ends 28,30,32 and 34 of the monofilaments with pressure pads which are mounted on swing arms and moving bending the length of monofilament and bring the outboard ends of the monofilaments together into side-by-side closely packed relationship as a bundle 68 as seen in FIGS. 3C and 3D. Thereupon the bundle of inboard ends of the monofilaments are inserted into the open end of the hollow tube and bonded within the tube as by sonic welders 138,140.

It is noted that the end 16 of the stem 12 defines a flat circumferential surface 130 (FIG. 3D). Thus, when the bundle 68 of monofilament ends is inserted into the tube, this shoulder defines a tactile sensory location for a used to position their thumb and finger(s) when grasping the appliance for use thereof in cleaning an ear canal. In this manner the presence of the user's thumb and finger(s) on the stem serve to limit the extent of insertion of the head 17 into an ear canal.

Whereas the dimensions of the stem and the head set forth herein as preferred, it will be understood that variations in these dimensions which do not materially alter the functioning of the appliance may be employed. Further, other methods of manufacture of the appliance may be employed. For example, the grooves depicted in FIG. 3A may be cylindrical holes drilled through the die 91. Still further, the size of the solidified mass of thermoplastic material and the extent of lateral flow thereof along each of the monofilaments may be adjusted through selection of the size of the horn of the sonic sealer and/or the amount of pressure applied to the molten thermoplastic at the intersection of the monofilaments. Other modifications or variations of the disclosed elements of the present invention will be evident to one skilled in the art, given the present description of the invention.

What is claimed:

1. An appliance for ear cleaning comprising
   an elongated hollow tube defining a stem having at least one open end,
   a plurality of lengths of monofilament, each having an outboard end and an inboard end, a mass of thermoplastic bonding each of said outboard ends of said monofilaments to one another with the respective ones of said plurality of lengths of said monofilaments at locations disposed substantially 90 degrees apart about the periphery of said mass and with each of said lengths of monofilament extending laterally away from said mass of thermoplastic, said mass of thermoplastic extending laterally thereof onto each of said outboard ends of said lengths of monofilament thereby imparting enhanced resistance to bending of each of said plurality of lengths of monofilaments within that region adjacent their respective outboard ends which are bonded to said mass, leaving the unbonded remainder of each of said plurality of lengths of monofilaments free to bend along their unbonded lengths, each of said plurality of lengths of monofilaments being bent along its length to the extent that each of said inboard ends of each of said plurality of lengths of monofilament are gathered together in side-by-side, closely-packed, relationship, whereby each of said plurality of lengths of monofilament are bent toward a common location thereby causing said unbonded remainder of each length of monofilament to bend against the aforesaid resistance with concomitant outwardly bulging of said unbonded remainder of each length of monofilament, said gathered inboard ends of said lengths of monofilaments being received with said at least one open end of said stem, means bonding said gathered inboard ends of said lengths of monofilaments within said at least one open end of said stem, thereby defining a bulbous configuration of said plurality of lengths of monofilaments.

2. The appliance of claim 1 wherein said stem of about 6 cm in length.

3. The appliance of claim 1 wherein said stem is formed of polypropylene.

4. The appliance of claim 1 wherein each of said plurality of lengths of monofilament each is of between about 18 and 25 gauge.

5. The appliance of claim 1 wherein said plurality of lengths of monofilament are defined by first and second lengths of monofilament which intersect each other at their respective midpoints and at mutually perpendicular directions and are bonded to one another at their junction of intersection with said bond extending laterally from said respective midpoints and alone a portion of the length of each of said plurality of lengths of monofilament.

6. The appliance of claim 5 wherein said intersecting monofilaments are bonded by a mass of thermoplastic which extends laterally away from said junction of intersection and along each of said monofilaments within the region thereof adjacent said juncture of intersection.

7. The appliance of claim 6 wherein said mass of thermoplastic is defined by melting and solidification of said intersecting monofilaments at said juncture of intersection of said intersecting monofilaments.

* * * * *